United States Patent [19]

Zeiss

[11] Patent Number: 5,420,329
[45] Date of Patent: May 30, 1995

[54] PROCESS FOR THE PREPARATION OF L-PHOSPHINOTHRICIN AND ITS DERIVATIVES

[75] Inventor: Hans-Jaochim Zeiss, Sulzbach/Taunus, Germany

[73] Assignee: Hoechst Aktiengesellschaft, Frankfurt am Main, Germany

[21] Appl. No.: 279,709

[22] Filed: Jul. 25, 1994

Related U.S. Application Data

[63] Continuation of Ser. No. 988,736, Dec. 10, 1992, abandoned.

[30] Foreign Application Priority Data

Dec. 13, 1991 [DE] Germany ............... 41 41 042.4

[51] Int. Cl.$^6$ .................... C07F 9/30; C07F 9/32
[52] U.S. Cl. ................... 558/137; 558/169; 558/170; 558/172; 562/11; 562/15
[58] Field of Search .......................... 558/137

[56] References Cited

U.S. PATENT DOCUMENTS

| | | |
|---|---|---|
| 4,168,963 | 9/1979 | Rupp et al. |
| 4,265,654 | 5/1981 | Takematsu et al. |
| 4,499,027 | 2/1985 | Minowa et al. |
| 4,777,279 | 10/1988 | Zeiss ................... 558/145 |

FOREIGN PATENT DOCUMENTS

| | | |
|---|---|---|
| 1161861 | 2/1984 | Canada . |
| 0018415 | 11/1980 | European Pat. Off. . |
| 0127429 | 12/1984 | European Pat. Off. . |
| 0238954 | 9/1987 | European Pat. Off. . |
| 0346658 | 12/1989 | European Pat. Off. . |
| 2717440 | 12/1977 | Germany . |
| 2856260 | 7/1979 | Germany . |
| 3525267 | 3/1986 | Germany . |
| 3542645 | 6/1987 | Germany . |
| 3609818 | 9/1987 | Germany . |
| 89/4019 | 5/1989 | South Africa . |

OTHER PUBLICATIONS

Sci. Reports of Meiji Seika Kaisha No. 20, pp. 33–38 (1981).

*Primary Examiner*—Mary C. Lee
*Assistant Examiner*—Michael G. Ambrose
*Attorney, Agent, or Firm*—Curtis, Morris & Safford

[57] ABSTRACT

The invention relates to a process for the enantioselective preparation of L-phosphinothricin (L-Ptc) and derivatives of the formula I

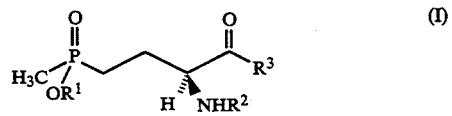

in which $R^1$ is H, $(C_1-C_6)$-alkyl, $(C_1-C_4)$-haloalkyl, $(C_3-C_6)$-cycloalkyl or (subst.) phenyl-$(C_1-C_4)$-alkyl, $R^2$ is hydrogen, formyl, [$(C_1-C_6)$alkyl]carbonyl, [$(C_1-C_6)$alkoxy]carbonyl, (subst.) benzyloxycarbonyl, $(C_1-C_6)$-alkylsulfonyl or (subst.) $(C_6-C_{10})$-arylsulfonyl, and $R^3$ is OH, $NH_2$ or $(C_1-C_6)$-alkoxy, or their salts with acids or bases.

20 Claims, No Drawings

PROCESS FOR THE PREPARATION OF L-PHOSPHINOTHRICIN AND ITS DERIVATIVES

This application is a continuation of application Ser. No. 07/988,736, filed Dec. 10, 1992, now abandoned.

The invention relates to a process for the enantioselective preparation of L-homoalanin-4-yl(methyl)phosphinic acid, called L-phosphinothricin or L-Ptc in the following, and its derivatives of the formula I

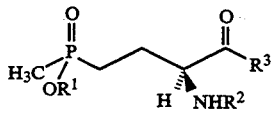

in which
- $R^1$ is hydrogen, $(C_1-C_6)$-alkyl, $(C_1-C_4)$-haloalkyl, $(C_3-C_6)$-cycloalkyl or phenyl-$(C_1-C_4)$-alkyl which is unsubstituted or substituted in the phenyl radical,
- $R^2$ is hydrogen, formyl, $[(C_1-C_6)alkyl]$carbonyl, $[(C_1-C_6)alkoxy]$carbonyl, benzyloxycarbonyl which is unsubstituted or substituted in the benzyl radical, $(C_1-C_6)$-alkylsulfonyl, or $(C_6-C_{10})$-arylsulfonyl which is unsubstituted or substituted in the aryl radical, and
- $R^3$ is hydroxyl, amino or $(C_1-C_6)$-alkoxy, or their salts with inorganic or organic acids or bases.

L-phosphinothricin, its esters and its salts with organic or inorganic acids or bases are the active enantiomers of the herbicidally active racemates described in DE-A-2,717,440. According to DE-A-2,856,260, the herbicidal action of L-Ptc is twice as great as that of the racemate, which is why the use of the L-isomer offers clear advantages, in particular economical and ecological advantages, which result from the lower application rates, lower amounts of formulation auxiliaries and as a result less substances to be broken down biologically in the soil and in the plants.

L-phosphinothricin has only been accessible until now by means of complicated, enzymatic resolution processes (DE-A-2,939,269; DE-A-3,048,612; EP-A-301,391; EP-A-358,428; EP-A-382,113; J. Chem. Soc. Perkin Trans 1989, 125) or by means of enzymatic transamination (EP-A-248,357, EP-A-249,188; Appl. Environ. Microbiol. 56 (1990) 1).

In addition to these biochemical methods, chemical processes for the preparation of L-Ptc are also known which, however, are afflicted with various disadvantages. Thus, with the aid of the enantioselective alkylation of chiral Schiff bases described in EP-A-127,429, as a rule only optical yields up to 78% are achieved, while the enantioselective hydrogenation of 2,3-didehydroamino acid derivatives described in DE-A-3,609,818 requires poorly accessible starting materials.

In addition, a further two methods are known which start from heterocyclic precursors which, however, can only be prepared in multi-step, complicated syntheses (DE-A-3,542,645; DE-A-3,525,267).

The object was therefore to develop a process which, in a simple manner, permits the preparation of L-phosphinothricin and its derivatives with high optical purity even in relatively large amounts.

The present invention thus relates to a process for the preparation of compounds of the formula I, which comprises a) reacting an L-vinylglycine derivative of the formula II with a methanephosphonous acid monoester of the formula III

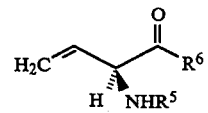

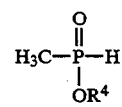

in which
- $R^4$ is defined as the radical $R^1$, excepting hydrogen, and
- $R^5$ is defined as the radical $R^2$, excepting hydrogen, and
- $R^6$ is $(C_1-C_6)$alkoxy, in the presence of a catalytic amount of a free radical initiator at reaction temperatures from 70° C. to 115° C. to give compounds Ia of the formula I, in which
- $R^1$ is defined as the radical $R^4$,
- $R^2$ is defined as the radical $R^5$ and
- $R^3$ is defined as the radical $R^6$, and b) if desired converting the compounds Ia obtained according to step a) analogously to customary methods from the group comprising hydrolysis and aminolysis processes into structurally different compounds Ib of the formula I, in which
- $R^1$ is defined as the radical $R^4$ or is hydrogen,
- $R^2$ is defined as the radical $R^5$ or is hydrogen and
- $R^3$ is defined as the radical $R^6$ or is hydroxyl or amino, and c) if desired converting the compounds Ia or Ib obtained according to step a) or b) into salts of the corresponding compounds of the formula I using inorganic or organic acids or bases.

In the formula (I) and in the following, the radicals alkyl and alkoxy as well as the alkyl and alkoxy radicals in the corresponding substituted radicals can each be straight-chain or branched. If not specifically stated, the carbon atom chains or carbon skeletons having 1 to 4 carbon atoms are preferred in these radicals. Alkyl radicals, also in the compound meanings such as alkoxy, alkylsulfonyl etc., are methyl, ethyl, n- or i-propyl, or n-, i-, t- or 2-butyl. Halogen is fluorine, chlorine, bromine or iodine; haloalkyl is alkyl which is substituted by one or more atoms from the halogen group; haloalkyl is, for example, $CF_3$, $CHF_2$ or $CH_2CF_3$. Aryl is, for example, phenyl, naphthyl, tetrahydronaphthyl, indenyl, indanyl and similar radicals, preferably phenyl; in the case of substituted aryl, phenyl or benzyl, the substituents are preferably each one or more, in particular 1, 2 or 3, radicals from the group comprising halogen, alkyl, haloalkyl, alkoxy, haloalkoxy, nitro, cyano, alkoxycarbonyl, alkylcarbonyl, alkanoyl, carbamoyl, mono- and dialkylaminocarbonyl, mono- and dialkylamino, alkylsulfinyl and alkylsulfonyl; here in the case of radicals having carbon atoms those having 1 to 4 carbon atoms, in particular 1 or 2 carbon atoms, are preferred; preferred substituents are, as a rule, those from the group comprising halogen, such as fluorine and chlorine, $C_1-C_4$-alkyl, preferably methyl or ethyl, $C_1-C_4$-haloalkyl, preferably trifluoromethyl, $C_1-C_4$-alkoxy, preferably methoxy or ethoxy, $C_1-C_4$-haloalkoxy, nitro and cyano. Methyl, methoxy and chlorine are particularly preferred.

Of particular interest are processes according to the invention, in which in formula I $R^1$ is hydrogen, ($C_1$-$C_6$)-alkyl, cyclopentyl, cyclohexyl or benzyl, $R^2$ is hydrogen, formyl, [($C_1$-$C_4$)alkyl]carbonyl, [($C_1$-$C_4$)alkoxy]carbonyl, benzyloxycarbonyl, ($C_1$-$C_4$)-alkylsulfonyl, or phenylsulfonyl which is unsubstituted or substituted in the phenyl radical, and $R^3$ is hydroxyl, amino or ($C_1$-$C_6$) -alkoxy.

Processes according to the invention are preferred, in which in formula I $R^1$ is hydrogen or ($C_1$-$C_4$) -alkyl, $R^2$ is hydrogen, [($C_1$-$C_4$)alkyl]carbonyl, [($C_1$-$C_4$)alkoxy]carbonyl or benzyloxycarbonyl, and $R^3$ is hydroxyl, amino or ($C_1$-$C_4$)-alkoxy.

As free radical initiators, for example, compounds can be used which dissociate into free radicals in the temperature range from 70°–115° C., such as, for example, t-butyl perbenzoate, t-butyl perpivalate, t-butyl perethylhexanoate, t-butyl perneodecanoate or azobisisobutyronitrile or mixtures of two or more of these compounds. Ultraviolet radiation can also be employed for the formation of the free radicals.

The optical yields are usually greater than 90%, which corresponds to a content of at least 95% of the L-enantiomer.

Additions of methanephosphonous acid monoesters to functionalized olefins for the preparation of phosphinothricin and its derivatives are admittedly known in principle, but the processes described are afflicted with various disadvantages.

Thus, EP-A-18,415 describes the reaction of racemic vinylglycine derivatives with methanephosphonous acid monoesters, reaction temperatures of at least 140° C. admittedly being used in the exemplary embodiments. In the case of optically active compounds of said formula II, reaction conditions of this type lead to partial or substantial racemization.

Furthermore, it is pointed out in Sci. Rep. of Meiji Seika Saisha 20 (1981) pages 33 et seq. that if compounds of said formula II are employed in which $R^5$ is acetyl or benzoyl and $R^6$ is hydroxyl, at reaction temperatures from 130° to 140° C. an isomerization of the compounds of the formula II to give compounds of the formula IV occurs:

Only if $R^5$ is an electron-withdrawing group such as trifluoromethyl is the amount of isomerization negligibly low. The known process is therefore not suitable for the enantioselective synthesis of compounds of said formula I.

Surprisingly, the free radical addition reaction takes place in the process according to the invention in an effective manner at appreciably lower temperature. It was also not to be expected that the reaction would proceed virtually without racemization.

The reaction of cyclic L-vinylglycine derivatives with methanephosphonous acid monoesters is the subject matter of EP-A-346,658. Admittedly, the optical purities for L-Ptc described there of over 90% are satisfactory but, depending on the starting material used, the preparation of L-Ptc derivatives can only be effected in a complicated manner via several steps.

In contrast, the process according to the invention can be carried out with easily accessible starting materials. In addition, the compounds of the formula I obtained in step a) (compounds Ia) can be converted by simple, acidic hydrolysis into the free amino acid L-Ptc or its hydrochloride.

Process step a) is carried out, for example, by adding the compound of the formula II and 0.1 to 20 mol %, preferably 0.5 to 10 mol %, of the free radical initiator, relative to the compound of the formula II, to a 1.5- to 4-fold excess of methanephosphonous acid monoester, which is heated to reaction temperature. The addition should preferably take place in such a way that as low as possible a stationary concentration of compound of the formula II is established.

In step a) the reaction temperature is 70° to 115° C., preferably 80° to 110° C., in particular 80° to 110° C. The reaction is preferably carried out in undiluted form, i.e. without additional solvent, in step a). If compound II is a solid or a highly viscous liquid, it may be advantageous to dissolve this in an inert solvent together with the free radical initiator. Suitable inert solvents should not react or only react to the smallest possible extent with the free radicals under the reaction conditions. Such solvents are, for example, unbranched hydrocarbons, such as n-pentane or n-hexane, or optionally halogenated, aromatic hydrocarbons, such as toluene, xylene or chlorobenzene.

To avoid undesired side-reactions, it is usually advisable to carry out the reaction in a protective gas atmosphere. Possible protective gases are, for example, nitrogen or argon.

In step a) the reaction time is as a rule between 0.25 and 3 hours, and the progress of the reaction can be monitored using customary analytical methods, such as gas chromatography or thin layer chromatography.

After reaction is complete, the excess methanephosphonous acid monoester III, if appropriate together with solvent, can be removed from the reaction product, for example by distillation. The crude reaction product of the formula Ia can be further purified by customary processes, such as, for example, crystallization or chromatography.

It is additionally surprising in the process according to the invention, besides the fact that no racemization or isomerization of the starting material of the formula II occurs, that no polymerization of the substituted vinyl compound of the formula II takes place, since the reaction conditions correspond to those of a free radical polymerization (cf. G. Henrici-Olive, S. Olive: Polymerisation, p. 1 et seq., Verlag Chemie, Weinheim 1969).

The compounds of said formula II are accessible by various routes in a simple manner from L-methionine (J. Org. Chem. 45 (1980) 4817; J. Org. Chem. 52 (1987) 4471; Chem. Pharm. Bull. 36 (1988) 893; J. Org. Chem. 52 (1988) 4074; Synth. Comm. 19 (1989) 3457) or L-glutamic acid (Tetrahedron Lett. 25 (1984) 1425; Tetrahedron 41 (1985) 4347; J. Org. Chem. 56 (1991) 728).

The compounds of the formula III are described in Houben-Weyl, Methoden der organischen Chemie (Methods of Organic Chemistry), volume XII/1, pp. 1, 5, 193 and 294 (1963), Georg Thieme Verlag, Stuttgart.

Process step b) can be used to convert the compounds of the formula I obtained in step a) into the compounds of the formula I in which at least one of the radicals $R^1$, $R^2$ and $R^3$ has one of the following meanings:

$R^1$ = hydrogen,
$R^2$ = hydrogen and
$R^3$ = hydroxyl or amino.

Process step c) can be used to convert the compounds Ia or Ib obtained in step a) or b) into salts. When carrying out step b), in most cases formation of the salt according to step c) can be carried out directly or simultaneously, so steps b) and c) are as a rule carried out as one-pot processes.

If, in process step b), a complete acidic or alkaline hydrolysis is used, the free amino acid L-phosphinothricin (L-Ptc) is obtained. Preferably, the hydrolysis is carried out using 3N–12N aqueous hydrochloric acid, particularly preferably using 5N–10N HCl. The reaction temperature is, for example, 90°–130° C., and the reaction time is as a rule 5–20 hours, but preferably 8–15 hours. After reaction is complete, the aqueous reaction solution is extracted for working up, for example with a water-immiscible solvent, such as toluene, xylene, dichloromethane or methyl isobutyl ketone, to remove the secondary products of the removal of the radicals $R^4$, $R^5$ and $R^6$.

The crude L-Ptc obtained after concentration of the aqueous solution, which is obtained as the hydrochloride when hydrochloric acid is used as described above, can be further purified by known measures such as recrystallization or ion exchange.

Derivatives of the formula I in which $R^3$ is amino are obtained when the compound Ia obtained in step a) is reacted, for example, with aqueous ammonia.

The following examples serve to illustrate the invention which, however, is not restricted thereby to the procedures described by way of example.

EXAMPLE 1

Methyl L-2-benzyloxycarbonylamino-4-[ethoxy(methyl)phosphinyl]butyrate 1.40 g (13.2 mmol) of monoethyl methanephosphonite are heated to 95° C. under an argon atmosphere. A mixture of 1.10 g (4.4 mmol) of methyl L-2-benzyloxycarbonylamino-3-butenoate and 0.032 g (0.15 mmol) of t-butyl perethylhexanoate in 3.5 ml of xylene is added dropwise in the course of 10 min at this temperature. The reaction mixture is stirred for a further 1 hour at 95° C., then all the volatile compounds are distilled off in a high vacuum. The crude product thus obtained is purified by chromatography on silica. gel (eluent: dichloromethane/methanol). 0.90 g (57.4% of theory) of methyl L-2-benzyloxycarbonylamino-4-[ethoxy(methyl)phosphinyl]butyrate is obtained as a colorless oil.

$[\alpha]_D^{23} = +10.90°$ (c=0.4550, CHCl$_3$)

$^1$H-NMR (100 MHz, CDCl$_3$) $\delta$ = 7.35 (s, 5, C$_6$H$_5$); 5.65 (s, br, 1, CHNHCOO); 5.10 (s, 2, OCH$_2$C$_6$H$_5$); 4.42 (m, 1, CHNHCOO); 4.03 (qd, 2, J=7 Hz, J=2 Hz, H$_3$CCH$_2$OP); 3.75 (s, 3, COOCH$_3$); 2.39–1.55 (m, 4, PCH$_2$CH$_2$CH); 1.43 (d, 3, J=14 Hz, PCH$_3$); 1.30 (dt, 3, J=2 Hz, J=7 Hz, POCH$_2$CH$_3$).

$^{31}$P-NMR (121 MHz, CDCl$_3$) $\delta$ = 54,075.

As can be seen from the $^1$H NMR spectrum, the sample contains 1 mol of water which cannot be removed even by drying for 14 days over P$_2$O$_5$.

CHN analysis: C$_{16}$H$_{24}$NO$_6$P × 1 H$_2$O: Calc.: C, 51.19; H, 6.98; N, 3.73. Found: C, 51.60; H, 6.60; N, 3.40.

EXAMPLE 2

Methyl L-2-benzyloxycarbonylamino-4-[n-butoxy(methyl)phosphinyl]butyrate

Starting from 1.88 g (13.8 mmol) of n-butyl methanephosphonite and 1.15 g (4.6 mmol) of methyl L-2-benzyloxycarbonylamino-3-butenoate, 1.22 g (68.8% of theory) of methyl L-2-benzyloxycarbonylamino-4-[n-butoxy(methyl)phosphinyl]butyrate are obtained under the conditions mentioned in Example 1 as a colorless oil.

$[\alpha]_D^{23} = +10.10°$ (c=0,662, CHCl$_3$)

$^1$H-NMR (100 MHz, CDCl$_3$) $\delta$ = 7.34 (s, 5, C$_6$H$_5$); 5.68 (s, br, 1, CHNHCOO); 5.09 (s, 2, OCH$_2$C$_6$H$_5$); 4.39 (m, 1, CHNHCOO); 3.94 (m, J=7 Hz, J=2 Hz, CH$_2$CH$_2$OP); 3.72 (s, 3, COOCH$_3$); 2.40–1.14 (m, 8, PCH$_2$CH$_2$CH and H$_3$CCH$_2$CH$_2$CH$_2$O); 1.43 (d, 3, J=14 Hz, PCH$_3$); 0.90 (m, 3, POCH$_2$CH$_2$CH$_2$CH$_3$).

$^{31}$P-NMR (121 MHz, CDCl$_3$) $\delta$ = 54.107.

EXAMPLE 3

L-Phosphinothricin hydrochloride 0.69 g (1.93 mmol) of methyl L-2-benzyloxycarbonylamino-4-[ethoxy(methyl)phosphinyl]butyrate (from Example 1) are dissolved in 10 ml of 6N HCl and heated under reflux for 10.5 hours. After cooling to room temperature, the aqueous solution is extracted twice with 3 ml of dichloromethane each time and the aqueous phase is then concentrated to dryness. 0.35 g (83.3% of theory) of L-phosphinothricin hydrochloride is obtained as a residue, which is identified by its $^1$H NMR spectrum.

$[\alpha]_D^{23} = +20.10°$ (c=1.860, 1N HCl)

The enantiomer excess, which was determined with the aid of an HPLC method [J. Chromatogr. 368, 413, (1986)] is 92.6%.

I claim:

1. A process for the preparation of a compound of formula I or a salt thereof

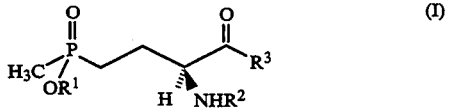

in which
$R^1$ is hydrogen, (C$_1$–C$_6$)-alkyl, (C$_1$–C$_4$)-haloalkyl, (C$_3$–C$_6$)-cycloalkyl or phenyl-(C$_1$–C$_4$)-alkyl which is unsubstituted or substituted in the phenyl radical,
$R^2$ is hydrogen, formyl, [(C$_1$–C$_6$)alkyl]carbonyl, [(C$_1$–C$_6$)alkoxy]carbonyl, benzyloxycarbonyl which is unsubstituted or substituted in the benzyl radical, (C$_1$–C$_6$)-alkylsulfonyl, or (C$_6$–C$_{10}$)-arylsulfonyl which is unsubstituted or substituted in the aryl radical, and
$R^3$ is hydroxyl, amino or (C$_1$–C$_6$)-alkoxy,
which process comprises a) reacting an L-vinylglycine derivative of the formula II with a methanephosphonous acid monoester of the formula III

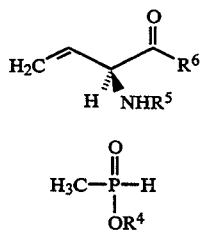

(II)

(III)

in which

R$^4$ is defined as the radical R$^1$, excepting hydrogen, and

R$^5$ is defined as the radical R$^2$, excepting hydrogen, and

R$^6$ is (C$_1$–C$_6$)alkoxy, in the presence of a catalytic amount of a free radical initiator selected from the group consisting of t-butyl perbenzoate, t-butyl perpivalate, t-butyl perethylhexanoate, t-butyl perneodecanoate or azobisisobutyronitrile and mixtures thereof, at reaction temperatures from 70° C. to 115° C. to give a compound of formula Ia,

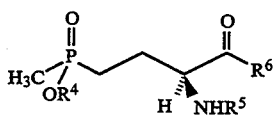

(Ia)

in which R$^4$, R$^5$ and R$^6$ are as defined above and,
b) if desired converting the compound Ia obtained according to step a) by a method comprising hydrolysis or aminolysis into a structurally different compound of the formula I, in which
R$^1$ is as defined above,
R$^2$ is as defined above and
R$^3$ is as defined above, and
c) if desired converting the compound obtained according to step a) or b) into a salt of the corresponding compound of the formula I using an inorganic or organic acid or base.

2. The process as claimed in claim 1, wherein
R$^1$ is hydrogen, (C$_1$–C$_6$)-alkyl, cyclopentyl, cyclohexyl or benzyl,
R$^2$ is hydrogen, formyl, [(C$_1$–C$_4$)alkyl]carbonyl, [(C$_1$–C$_4$)alkoxy]carbonyl, benzyloxycarbonyl, (C$_1$–C$_4$)-alkylsulfonyl, or phenylsulfonyl which is unsubstituted or substituted in the phenyl radical, and
R$^3$ is hydroxyl, amino or (C$_1$–C$_6$)-alkoxy.

3. The process as claimed in claim 1 wherein
R$^1$ is hydrogen or (C$_1$–C$_4$)-alkyl,
R$^2$ is hydrogen, [(C$_1$–C$_4$)alkyl]carbonyl, [(C$_1$–C$_4$)-alkoxy]carbonyl or benzyloxycarbonyl, and
R$^3$ is hydroxyl, amino or (C$_1$–C$_4$)-alkoxy.

4. The process as claimed in claim 1, wherein reaction temperatures of 80° to 110° C. are used in step a).

5. The process as claimed in claim 1, wherein the free radical initiator is added in amounts of 0.1 to 20 mol %, relative to the compound of the formula II.

6. The process as claimed in claim 5, wherein the free radical initiator is added in amounts of 0.5 to 10 mol %, relative to the compound of the formula II.

7. The process as claimed in claim 1, wherein aqueous 3N–12N hydrochloric acid is used in process step b) for hydrolysis.

8. The process as claimed in claim 7, wherein aqueous 5N–10N hydrochloric acid is used in process step b) for hydrolysis.

9. The process as claimed in claim 7, wherein a reaction temperature of 90° to 130° C. is used in process step b).

10. The process as claimed in claim 1, wherein the free radical initiator is added in amounts of 0.1 to 20 mol %, relative to the compound of formula II.

11. The process as claimed in claim 10, wherein the 0.5 to 10 mol % are added.

12. The process as claimed in claim 10, wherein reaction temperatures of 80° to 110° C. are used in step a).

13. The process as claimed in claim 11, wherein reaction temperatures of 80° to 110° C. are used in step a).

14. The process as claimed in claim 13, wherein
R$^1$ is H or (C$_1$–C$_4$)alkyl,
R$^2$ is H, [(C$_1$–C$_4$)alkyl]carbonyl, [(C$_1$–C$_4$)alkoxy]carbonyl or benzyloxycarbonyl, and
R$^3$ is OH, NH$_2$ or (C$_1$–C$_4$)alkoxy.

15. The process as claimed in claim 14, wherein aqueous 5N–10N HCl is used in process step b) at a temperature of 90° to 130° C.

16. The process as claimed in claim 1, wherein the temperatures of 70° to 95° C. are used in step a).

17. The process as claimed in claim 1, wherein the temperatures of 80° to 95° C. are used in step a).

18. The process as claimed in claim 3, wherein the free radical initiator is t-butyl perethyl-hexanoate.

19. The process as claimed in claim 6, wherein the free radical initiator is t-butyl perethyl-hexanoate.

20. The process as claimed in claim 16, wherein the free radical initiator is t-butyl perethyl-hexanoate.

* * * * *

UNITED STATES PATENT AND TRADEMARK OFFICE
CERTIFICATE OF CORRECTION

PATENT NO. : 5,420,329
DATED : May 30, 1995
INVENTOR(S) : Hans-Joachim Zeiss

It is certified that error appears in the above-indentified patent and that said Letters Patent is hereby corrected as shown below:

On the title page item [75], delete --Hans-Jaochim Zeiss--, insert --Hans-Joachim Zeiss--.

Signed and Sealed this

Twenty-sixth Day of December, 1995

Attest:

BRUCE LEHMAN

*Attesting Officer*    *Commissioner of Patents and Trademarks*